United States Patent
Ragheb

(10) Patent No.: US 12,324,826 B2
(45) Date of Patent: Jun. 10, 2025

(54) COMPOSITIONS AND METHODS TO MITIGATE OR PREVENT AN IMMUNE RESPONSE TO AN IMMUNOGENIC THERAPEUTIC MOLECULE IN NON-HUMAN PRIMATES

(71) Applicant: Jomoco, Corp, Bethesda, MD (US)

(72) Inventor: Jack A. Ragheb, N. Bethesda, MD (US)

(73) Assignee: JOMOCO, Corp., Bethesda, MD (US)

(*) Notice: Subject to any disclaimer, the term of this patent is extended or adjusted under 35 U.S.C. 154(b) by 434 days.

(21) Appl. No.: 17/366,824

(22) Filed: Jul. 2, 2021

(65) Prior Publication Data

US 2021/0330746 A1 Oct. 28, 2021

Related U.S. Application Data

(60) Division of application No. 16/138,787, filed on Sep. 21, 2018, now Pat. No. 11,083,778, which is a continuation of application No. 15/368,125, filed on Dec. 2, 2016, now abandoned.

(60) Provisional application No. 62/263,352, filed on Dec. 4, 2015.

(51) Int. Cl.
| | |
|---|---|
| *A61K 38/20* | (2006.01) |
| *C07K 14/715* | (2006.01) |
| *C07K 16/28* | (2006.01) |
| *A61K 31/436* | (2006.01) |
| *A61K 39/00* | (2006.01) |
| *A61K 45/06* | (2006.01) |

(52) U.S. Cl.
CPC ...... *A61K 38/2013* (2013.01); *C07K 14/7155* (2013.01); *C07K 16/2866* (2013.01); *A61K 31/436* (2013.01); *A61K 2039/505* (2013.01); *A61K 45/06* (2013.01); *C07K 2317/76* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,289,872 A | 9/1981 | Denkewalter et al. |
| 4,411,993 A | 10/1983 | Gillis |
| 4,473,493 A | 9/1984 | Gillis |
| 4,772,572 A | 9/1988 | Yoshimoto et al. |
| 4,845,198 A | 7/1989 | Urdal et al. |
| RE33,252 E | 7/1990 | Gillis |
| 5,229,490 A | 7/1993 | Tam |
| 5,314,995 A | 5/1994 | Fell, Jr. et al. |
| 5,543,158 A | 8/1996 | Gref et al. |
| 5,889,160 A | 3/1999 | Sugamura et al. |
| 6,168,785 B1 | 1/2001 | Theze et al. |
| 6,383,487 B1 | 5/2002 | Amlot et al. |
| 6,521,230 B1 | 2/2003 | Amlot et al. |
| 6,596,853 B1 | 7/2003 | Theze et al. |
| 6,998,391 B2 | 2/2006 | Lyons et al. |
| 7,078,034 B2 | 7/2006 | Lamb, Jr. |
| 7,423,113 B2 | 9/2008 | Tavernier et al. |
| 7,438,907 B2 | 10/2008 | Schuurman et al. |
| 7,579,439 B2 | 8/2009 | Strom et al. |
| 8,182,812 B2 | 5/2012 | Schuurman et al. |
| 8,465,739 B2 | 6/2013 | Kaisheva et al. |
| 8,592,368 B2 | 11/2013 | Mohapatra |
| 8,759,486 B2 | 6/2014 | Monzon et al. |
| 8,895,544 B2 | 11/2014 | Coe et al. |
| 8,961,968 B2 | 2/2015 | Schuurman et al. |
| 9,028,830 B2 | 5/2015 | Tso et al. |
| 9,109,026 B2 | 8/2015 | Ghayur et al. |
| 9,133,200 B2 | 9/2015 | Gonzalez Rodriguez et al. |
| 9,133,268 B2 | 9/2015 | Govindan |

(Continued)

FOREIGN PATENT DOCUMENTS

| | | |
|---|---|---|
| EP | 0036676 | 9/1981 |
| EP | 0058481 | 8/1982 |

(Continued)

OTHER PUBLICATIONS

Vajdos et al. (J Mol Biol. Jul. 5, 2002;320(2):415-28 (Year: 2002).*
Brown et al. (J Immunol. May 1996; 156(9):3285-91 (Year: 1996).*
Tinubu et al (J Immunol (1994) 153 (9): 4330-4338) (Year: 1994).*
Montgomery et al, American Journal of Transplantation 2002; 2: 381-385 (Year: 2002).*
Aagaard et al. (2007) "RNAi Therapeutics: Principles, Prospects and Challenges" Advanced Drug Delivery Reviews 59(2):75-86.
Baldrick (2011) "Safety evaluation of biological drugs: what are toxicology studies in primates telling US? " Regulatory Toxicology and Pharmacology 59(2):227-326.
Bayle et al. (2006) "Rapamycin Analogs with Differential Binding Specificity Permit Orthogonal Control of Protein Activity" Chemistry & Biology 13:99-107.
Bowie et al. (1990) "Deciphering the Message in Protein Sequences: Tolerance to Amino Acid Substitutions" Science 247(4948):1306-1310.

(Continued)

*Primary Examiner* — Brian Gangle
*Assistant Examiner* — Andrea K McCollum
(74) *Attorney, Agent, or Firm* — FisherBroyles, LLP; Cara L. Crowley-Weber

(57) ABSTRACT

Methods and compositions for preventing an immune response to an immunogenic therapeutic agent [i.e. anti-drug antibody (ADA), a.k.a. anti-therapeutic antibody (ATA)] are disclosed. One of the disclosed methods comprises administering an effective amount of an immunosuppressant such as an Interleukin-2 (IL-2) signaling pathway inhibitor, including an antagonist, super agonist or partial agonist to the cytokine IL-2, to the IL-2 receptor (IL-2R), or to IL-2R signal transduction molecules. Inhibitors can be in the form of antibodies or antibody fragments, peptide inhibitors, fusion molecule, small molecules, antibody/small molecule conjugates. Administration of a given inhibitor can decrease the incidence and/or magnitude of an immune response or prevent an immune response, including an antibody response, to a potentially immunogenic therapeutic agent in a non-human primate (NHP). Some of the disclosed methods produce a tolerizing effect in NHPs.

14 Claims, No Drawings

(56) References Cited

U.S. PATENT DOCUMENTS

| | | |
|---|---|---|
| 9,175,083 B2 | 11/2015 | Cho et al. |
| 9,180,182 B2 | 11/2015 | van Kooyk et al. |
| 2002/0086049 A1 | 7/2002 | Bolton et al. |
| 2006/0002852 A1 | 1/2006 | Saltzman et al. |
| 2006/0222652 A1 | 10/2006 | Sebbel et al. |
| 2006/0251677 A1 | 11/2006 | Bachmann et al. |
| 2007/0048293 A1 | 3/2007 | Turka et al. |
| 2008/0145441 A1 | 6/2008 | Penades et al. |
| 2009/0028910 A1 | 1/2009 | DeSimone et al. |
| 2009/0226525 A1 | 9/2009 | de los Rios et al. |
| 2013/0072482 A1 | 3/2013 | Yang et al. |
| 2014/0349323 A1 | 11/2014 | Essig et al. |
| 2015/0118229 A1 | 4/2015 | Voss et al. |
| 2015/0335762 A1 | 11/2015 | Fraser et al. |
| 2016/0256401 A1 | 9/2016 | Fraser et al. |

FOREIGN PATENT DOCUMENTS

| | | |
|---|---|---|
| EP | 0088046 | 2/1983 |
| EP | 0133988 | 8/1984 |
| EP | 0143949 | 6/1985 |
| WO | 1992016221 | 10/1992 |
| WO | 199315722 | 8/1993 |
| WO | 1993021259 | 10/1993 |
| WO | 1994020069 | 9/1994 |
| WO | 1995034326 | 12/1995 |
| WO | 1996032478 | 10/1996 |
| WO | 1997034631 | 9/1997 |
| WO | 2009051837 | 4/2009 |
| WO | 2009106999 | 9/2009 |
| WO | 2010047839 | 4/2010 |
| WO | 2015164815 | 10/2015 |

OTHER PUBLICATIONS

Bork (2000) "Powers and Pitfalls in Sequence Analysis: The 70% Hurdle" Genome Research 10(4):398-400.

Brennan et al. (2015) "Nonclinical safety testing of biopharmaceuticals—Addressing current challenges of these novel and emerging therapies" Regulatory Toxicology and Pharmacology 73(1):265-275.

Brown (1996) "Tolerance of Single, but not Multiple, Amino Acid Replacements in Antibody VH CDR 2: a Means of Minimizing B Cell Wastage from Somatic Hypermutation?" J. Immunol. 156(9):3285-3291.

Burgess (1990) "Possible Dissociation of the Heparin-Binding and Mitogenic Activities of Heparin-Binding (Acidic Fibroblast) Growth Factor-1 from its Receptor-Binding Activities by Site-Directed Mutagenesis of a Single Lysine Residue" J. Cell Biol. 111(5):2129-2138.

Chamberlain et al. (2003) "An Overview of Scientific and Regulatory Issues for the Immunogenicity of Biological Products" Immunogenicity of Therapeutic Biological Products, Dev. Biol. Basel, Karger 112:3-11.

Chang et al. (1999) "Evolution of a Cytokine Using DNA Family Shuffling" Nature Biotechnology 17:793-797.

Clark et al. (2014) "Discovery and Development of Janus Kinase (JAK) Inhibitors for Inflammatory Diseases" J. Med. Chem. 57(12):5023-5038.

Ellison et al. (1982) "The nucleotide sequence of a human immunoglobulin Cyl gene" Nucleic Acids Res. 10:4071-4079.

Eppstein et al. (1985) "Biological activity of liposome-encapsulated murine interferon gamma is mediated by a cell membrane receptor" PNAS 82:3688-3692.

Herzyk (2003) "The Immunogenicity of Therapeutic Cytokines" Current Opinion in Molecular Therapeutics 5(2):167-171.

Guido et al. (2008) "Virtual Screening and its Integration with Modern Drug Design Technologies" Curr. Med. Chem. 15(1):37-46.

International Search Report and Written Opinion for PCT/US2016/064770 dated May 1, 2017.

Isaacs (1990) "The Antiglobulin Response to Therapeutic Antibodies" Seminars in Immunology 2(6):449-456.

Kishimoto et al. (2016) "Improving the efficacy and safety of biologic drugs with tolerogenic nanoparticles" Nature Nanotechnology, 11:890-899 (Lined Through in Parent IDS).

Koren et al. (2002) "Immune Responses to Therapeutic Proteins in Humans—Clinical Significance, Assessment and Prediction" Current Pharmaceutical Biotechnology 3(4):349-360.

Kurtzman et al. (2001) "Advances in Directed Protein Evolution by Recursive Genetic Recombination: Applications to Therapeutic Proteins" Current Opinion in Biotechnology 12:361-370.

Langer et al. (1981) "Biocompatibility of polymeric delivery systems for macromolecules" J. Biomed. Mater. Res. 15:167-277.

Lazar et al. (1988) "Transforming Growth Factor Alpha: Mutation of Aspartic Acid 47 and Leucine 48 Results in Different Biological Activities" Mol. Cell Biol. 8(3):1247-1252.

Levin et al. (2012) "Exploiting a Natural Conformational Switch to Engineer an Interleukin-2 'Superkine'." Nature 484(7395):529-533 (PMID: 22446627).

Nechansky and Kircheis (2010) "Immunogenicity of therapeutics: a matter of efficacy and safety" Expert Opin Drug Discov. 5(11):1067-1079.

McKeague et al. (2012) "Challenges and Opportunities for Small Molecule Aptamer Development" J. Nucleic Acids 2012:748913 Epub.

Paolicelli et al. (2010) "Surface-modified PLGA-based Nanoparticles that can Efficiently Associate and Deliver Virus-like Particles" Nanomedicine. 5(6):843-853.

Porter (2001) "Human Immune Response to Recombinant Human Proteins" J. Pharmaceutical Sciences 90(1):1-11.

Rosenberg (2003) "Immunogenicity of Biological Therapeutics: A Hierarchy of Concerns" Immunogenicity of Therapeutic Biological Products, Dev. Biol. Basel, Karger 112:15-21.

Schellekens and Casadevall (2003) "Immunogenicity of Biopharmaceuticals. The European Perspective" Immunogenicity of Therapeutic Biological Products, Dev. Biol. Basel, Karger, 112:23-38.

Sidman et al. (1983) "Controlled release of macromolecules and pharmaceuticals from synthetic polypeptides based on glutamic acid" Biopolymers 22:547-556.

Stein (2002) "Immunogenicity: Concepts/Issues/Concerns" Biologics 2000 Comparability of Biotechnology Products Dev. Bio. Basel, Karger 109:15-23.

Swanson and Bussiere (2012) "Immunogenicity assessment in non-clinical studies" Curr Opin Microbiol. 15(3):337-347.

Thway et al. (2013) "Impact of anti-drug antibodies in preclinical pharmacokinetic assessment" Aaps J. 15(3):856-563.

Tsutsumi et a (2000) "Site-Specific Chemical Modification with Polyethylene Glycol of Recombinant Immunotoxin Anti-Tac(Fv)-PE38 (LMB-2) Improves Antitumor Activity and Reduces Animal Toxicity and Immunogenicity" PNAS 97(15):8548-8553.

Vajdos et al.(2002) "Comprehensive Functional Maps of the Antigen-Binding Site of an Anti-ErbB2 Antibody Obtained with Shotgun Scanning Mutagenesis" J. Mol. Biol. 320(2):415-428.

Warzocha et al. (1997) "Antisense Strategy: Biological Utility and Prospects in the Treatment of Hematological Malignancies" Leukemia and Lymphoma 24(3-4):267-281.

Xu et al. (2003) "Effects of Combined Treatment with CD25- and CD154-Specific Monoclonal Antibodies in Non-Human Primate Allotransplantation" American Journal of Transplantation 3(11):1350-1354.

* cited by examiner

COMPOSITIONS AND METHODS TO MITIGATE OR PREVENT AN IMMUNE RESPONSE TO AN IMMUNOGENIC THERAPEUTIC MOLECULE IN NON-HUMAN PRIMATES

RELATED APPLICATIONS

This application is a divisional of U.S. patent application Ser. No. 16/138,787, filed Sep. 21, 2018, now U.S. Pat. No. 11,083,778, issued Aug. 10, 2021, which is a continuation of U.S. patent application Ser. No. 15/368,125, filed Dec. 2, 2016, which claims priority under 35 U.S.C. 119 (e) to U.S. Provisional Patent Application Ser. No. 62/263,352, entitled "Compositions and Methods to Mitigate an Immune Response to an Immunogenic Therapeutic Agent in Non-Human Primates (NHP)", filed Dec. 4, 2015, the disclosure of which is hereby incorporated by reference in its entirety.

TECHNICAL FIELD

The present invention is generally in the field of immunology and of modulating responses to immunogenic therapeutic agents.

BACKGROUND OF THE INVENTION

Biological medicinal products and therapeutic agents are a growing proportion of tested pharmaceutical drugs. Drug development and licensure entails the testing of these products in several animal species prior to their administration to humans. As non-human primates (NHP) are the species closest to man, they are generally the last animal species in which testing is performed before a drug is administered to humans.

Biological medicinal products and therapeutic proteins are composed of amino acid sequences that are entirely human, partially human, or entirely non-human. In contrast to small drug molecules, these medicinal products elicit immune responses in the animal in which they are being tested.

Such immune responses occur in humans as well. Koren, et al., Current Pharmaceutical Biotechnology 3(4):349-360 (2002) present a table (table 1 at p. 352-3) detailing the incidence and clinical sequelae of antibody responses to some therapeutic proteins. Porter, supra, also provides a summary of the actual reported observations regarding human immune response to administered doses of recombinant human proteins.

Because the immune system of different species can distinguish orthologous proteins as foreign, the preclinical testing of human therapeutic proteins in non-human species can be dramatically hampered by the animals' immune response to the protein, resulting in antibody-mediated alterations of the proteins' activity, bioavailability or toxicity. Such antibodies may even trigger anaphylaxis or death of the animal. This is especially true when the protein is provided in multiple doses over a period of time. As a consequence, animals are typically sacrificed after a preclinical study that entails the single administration of the biological medicinal product.

During preclinical testing, the antibodies generated to the human biological therapeutic agent, so called anti-drug antibodies (ADA), can confound data on the pharmacokinetics and biodistribution of the agent under study. Such ADA can also alter or mask the toxicity of the agent, resulting in misguided interpretations of the predicted safety profile of the product in humans. As a consequence, the development of products that might have otherwise been halted during preclinical testing proceed into patients in Phase I clinical trials.

Methods that would prevent the development of ADA in animals are expected to produce more accurate pharmacokinetic and toxicity data, resulting in more efficient late stage drug development and safer Phase I studies of therapeutic biologicals in humans. Additionally, such methods would enable the reuse of NHP in preclinical studies of biological products, thus reducing the number of NHP sacrificed each year during drug testing.

Accordingly, there is a need for safe and effective compositions and methods to decrease undesired immune response and/or the probability of incidence of ADA to immunogenic therapeutic molecules, and to decrease antibody production when an undesired immune response occurs.

The present disclosure is directed toward overcoming one or more of the problems discussed above.

SUMMARY

Provided herein are methods for decreasing the probability of the incidence of undesired immune response and/or decreasing the intensity of an undesired immune response when a NHP is administered a therapeutic composition having an otherwise immunogenic therapeutic molecule.

In some embodiments, an undesired immune response may be the generation of ADA and/or lymphocyte proliferation, activation and/or effector functions.

Also provided herein are methods for decreasing the probability of the incidence of ADA and/or decreasing the intensity of ADA when a NHP is administered a therapeutic composition having an otherwise immunogenic therapeutic molecule.

The method includes administering to a NHP an effective amount of an effective form of an immunosuppressant within an effective time interval relative to the administration of the therapeutic composition having an otherwise immunogenic therapeutic molecule. The method includes administering to a NHP an effective amount of an effective form of an IL-2 pathway inhibitor within an effective time interval relative to the administration of the therapeutic composition.

In some embodiments, the immunosuppressant is selected from the group consisting of an IL-2 pathway inhibitor, a statin, an mTOR inhibitor, a TGF-β signaling agent, a corticosteroid, an inhibitor of mitochondrial function, a P38 inhibitor, an NF-κβ inhibitor, an adenosine receptor agonist, a prostaglandin E2 agonist, a phosphodiesterase 4 inhibitor, an HDAC inhibitor, and a proteasome inhibitor, or a combination thereof.

In some embodiments, the immunosuppressant is rapamycin or a rapamycin analog.

In some embodiments, the immunosuppressant is an anti-CD25 antibody such as basiliximab or a biosimilar thereof.

Also provided are compositions that include a therapeutic molecule capable of producing an immune response and an effective form of an IL-2 pathway inhibitor.

In some embodiments, administration of an immunosuppressant to an NHP as described herein decreases the probability of an incidence of ADA against an immunogenic therapeutic molecule. In some embodiments, administration of an immunosuppressant as described herein decreases the intensity of ADA formation against an immunogenic therapeutic molecule. In some embodiments, administration of an immunosuppressant to an NHP mitigates the formation of ADA in a NHP.

In some embodiments, administration of an IL-2 pathway inhibitor as described herein decreases the probability of an incidence of ADA against an immunogenic therapeutic molecule. In some embodiments, administration of an IL-2 pathway inhibitor as described herein decreases the intensity of ADA formation against an immunogenic therapeutic molecule. In some embodiments, administration of an IL-2 pathway inhibitor mitigates the formation of ADA in a NHP.

In some embodiments, administration of an immunosuppressant as described herein decreases the amount of antibodies generated to an immunogenic therapeutic molecule, thus lessening the severity of an immune reaction in a NHP.

In some embodiments, administration of an IL-2 pathway inhibitor as described herein decreases the amount of antibodies generated to an immunogenic therapeutic molecule, thus lessening the severity of an immune reaction in a NHP.

Also provided are methods for preventing an undesired immune response when a NHP is administered a therapeutic composition having an otherwise immunogenic therapeutic molecule. Prevention of such undesired immune response to the immunogenic therapeutic molecule is termed tolerance. Tolerance is recognized (i) when no immune response is generated even though therapeutic protein treatment continues and the immunosuppressant treatment is discontinued, and (ii) when the lack of immune response is specific to the therapeutic protein (i.e. treatment with a different therapeutic protein would generate an immune response).

In some embodiments, the immunosuppressant can be formulated to achieve an effective form, i.e. a form that elicits a tolerogenic immune response to an otherwise immunogenic therapeutic molecule. Such formulations can include synthetic nanocarriers.

In some embodiments, co-administration of two immunosuppressants, such as rapamycin and an IL-2 pathway inhibitor, can elicit a tolerogenic immune response to an otherwise immunogenic therapeutic molecule.

DESCRIPTION

As used herein, the term "statistically significant" has the same meaning it has in the art, e.g., that an observed effect is unlikely the result of mere chance. P values, or the like, may be used in this context, in which case a p<0.5 may indicate a statistically significant result. Other preferred p values include <0.2, <0.1, <0.05 and <0.01, although other p values may be used in accordance with accepted practices in the art.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described.

Immunosuppressants and Tolerogenic Agents

"Immunosuppressant" is intended to include agents that cause an Antigen Presenting Cell (APC) to have an immunosuppressive effect. An immunosuppressive effect generally refers to the production, or lack thereof, of cytokines or other factors by the APC that reduces, inhibits or prevents an undesired immune response. When APC activity results in an immunosuppressive effect on immune cells that recognize an antigen presented by the APC, the immunosuppressive effect is said to be specific to the presented antigen. Such effect is also referred to herein as a tolerogenic effect. For the purpose of this disclosure, the term "immunosuppressants" is intended to encompass those agents that prevent an immune response in an antigen non-specific manner and whose effect requires the continued administration of the immunosuppressant agent at a proscribed dose and schedule, as well as those agents that prevent an immune response in an antigen specific manner and whose effect does not require the continued administration of the agent, i.e. "tolerogenic" agents.

The immunosuppressive or tolerogenic effect is likely a result of the immunosuppressant being delivered to the APC, in some aspects, in the presence of an antigen (e.g., an administered antigen or one that is already present in vivo). Accordingly, the immunosuppressant includes compounds that provide a tolerogenic immune response to an antigen that may or may not be provided in the same composition or a different composition.

In one embodiment, the immunosuppressant is one that causes an APC to promote a regulatory phenotype in one or more immune effector cells. For example, the regulatory phenotype may be characterized by the inhibition of the production, induction, stimulation or recruitment of antigen-specific CD4+ T cells or B cells, the inhibition of the production of antigen-specific antibodies, the production, induction, stimulation or recruitment of Treg cells (e.g., CD4+ CD25highFoxP3+ Treg cells), etc. This may be the result of the conversion of CD4+ T cells or B cells to a regulatory phenotype. This may also be the result of induction of FoxP3 in other immune cells, such as CD8+ T cells, macrophages and iNKT cells. In one embodiment, the immunosuppressant is one that affects the response of the APC after it processes an antigen. In another embodiment, the immunosuppressant is not one that interferes with the processing of the antigen. In a further embodiment, the immunosuppressant is an apoptotic-signaling molecule. In another embodiment, the immunosuppressant is not a phospholipid.

Exemplary immunosuppressants include, but are not limited to, IL-2 pathway inhibitors; statins; mTOR inhibitors, such as rapamycin or a rapamycin analog; TGF-β signaling agents; TGF-β receptor agonists; histone deacetylase inhibitors, such as Trichostatin A; corticosteroids; inhibitors of mitochondrial function, such as rotenone; P38 inhibitors; NF-κβ inhibitors, such as 6Bio, Dexamethasone, TCPA-1, IKK VII; adenosine receptor agonists; prostaglandin E2 agonists (PGE2), such as Misoprostol; phosphodiesterase inhibitors, such as phosphodiesterase 4 inhibitor (PDE4), such as Rolipram; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3KB inhibitors, such as TGX-221; autophagy inhibitors, such as 3-Methyladenine; aryl hydrocarbon receptor inhibitors; proteasome inhibitor I (PSI); and oxidized ATPs, such as P2X receptor blockers. Immunosuppressants also include IDO, vitamin D3, cyclosporins, such as cyclosporine A, aryl hydrocarbon receptor inhibitors, resveratrol, azathiopurine (Aza), 6-mercaptopurine (6-MP), 6-thioguanine (6-TG), FK506, sanglifehrin A, salmeterol, mycophenolate mofetil (MMF), methotrexate, aspirin and other COX inhibitors, niflumic acid, estriol and triptolide. In certain embodiments, the immunosuppressant may comprise any of the agents provided herein.

In some embodiments, the immunosuppressant or inhibitor is a fully human recombinant protein; in some embodiments, the inhibitor is a fully primate recombinant protein. In some embodiments, the inhibitor is a human recombinant protein and at least a portion of the protein comprises a NHP sequence. In some embodiments, the inhibitor is a NHP recombinant protein and at least a portion of the protein comprises a human sequence. In some embodiments, the inhibitor is a human recombinant protein and at least a portion of the protein comprises a mouse sequence. In some embodiments, the inhibitor is a NHP recombinant protein and at least a portion of the protein comprises a mouse sequence.

The immunosuppressant can be a compound that directly provides the immunosuppressive or tolerogenic effect on APCs or it can be a compound that provides the immunosuppressive or tolerogenic effect indirectly (i.e., after being processed in some way after administration). Immunosuppressants, therefore, include prodrug forms of any of the compounds provided herein.

Immunosuppressants also include nucleic acids that encode the peptides, polypeptides or proteins provided herein that result in an immunosuppressive or tolerogenic immune response. In some embodiments, therefore, the immunosuppressant is a nucleic acid that encodes a peptide, polypeptide or protein that results in an immunosuppressive or tolerogenic immune response, and it is the nucleic acid that is coupled to the synthetic nanocarrier.

The nucleic acid may be DNA or RNA, such as mRNA. In embodiments, the inventive compositions comprise a complement, such as a full-length complement, or a degenerate (due to degeneracy of the genetic code) of any of the nucleic acids provided herein. In embodiments, the nucleic acid is an expression vector that can be transcribed when transfected into a cell line. In embodiments, the expression vector may comprise a plasmid, retrovirus, or an adenovirus amongst others. Nucleic acids can be isolated or synthesized using standard molecular biology approaches, for example by using a polymerase chain reaction to produce a nucleic acid fragment, which is then purified and cloned into an expression vector. Additional techniques useful in the practice of this invention may be found in Current Protocols in Molecular Biology, 2007, by John Wiley and Sons, Inc.; Molecular Cloning: A Laboratory Manual (Third Edition) Joseph Sambrook, Peter MacCallum Cancer Institute, Melbourne, Australia; David Russell, University of Texas Southwestern Medical Center, Dallas, Cold Spring Harbor.

Other exemplary immunosuppressants include, but are not limited to, small molecule drugs, natural products, antibodies (e.g., antibodies against CD20, CD3, CD4, CD25), biologics-based drugs, carbohydrate-based drugs, nanoparticles, liposomes, RNAi, antisense nucleic acids, aptamers, methotrexate, NSAIDs, fingolimod, natalizumab, alemtuzumab, anti-CD3, tacrolimus (FK506), etc. Further immunosuppressants are known to those of skill in the art, and the invention is not limited in this respect.

The term "IL-2" or "interleukin 2" refers to a protein having an amino acid sequence from a human, a cynomolgus macaque, or a rhesus macaque, for example. IL-2 is a cytokine signaling molecule which, upon binding the IL-2 receptor, initiates a plethora of effects on the immune system.

The phrase "IL-2 signaling pathway" refers to a ligand, a receptor, and the signal transduction pathway that is activated when the cytokine IL-2, or variants thereof, bind its receptor (IL-2R: CD25, CD122, and CD132) or variants thereof, leading to the activation of signaling molecules including, but not limited to, Jak1, Jak3, Stat5a, Stat5b, Lck, and Syk.

The phrase "IL-2 signaling pathway" is used interchangeably herein with "IL-2 pathway", and "IL-2 signal transduction pathway". Thus, any IL-2 inhibitor contemplated as useful in the methods provided herein is an IL-2 signaling pathway inhibitor, an IL-2 pathway inhibitor, and an IL-2 signal transduction pathway inhibitor.

The phrase "IL-2 signaling pathway inhibitor" refers to inhibitors that behave as antagonists or partial agonists to the cytokine IL-2, to the IL-2 receptor (IL-2R), or to the IL-2 signal transduction pathway. Inhibitors can be in the form of antibodies or antibody fragments, peptides, fusion molecules, soluble receptors, small molecules, and antibody/small molecule conjugates. Administration of a given inhibitor can decrease the incidence and/or magnitude of an antibody response to a potentially immunogenic therapeutic agent in a NHP. Administration of a given inhibitor can mitigate the formation of ADA in, for example, a NHP, administered a potentially immunogenic therapeutic agent. Administration of a given inhibitor in combination with rapamycin can prevent an undesired immune response, or can elicit a tolerogenic response in a NHP administered a potentially immunogenic therapeutic agent.

Thus, the IL-2 signaling pathway inhibitor can be, for example, an IL-2 cytokine antagonist, an IL-2 partial agonist, an IL-2 super agonist, an IL-2-chimeric fusion molecule, such as an IL-2-IgG fusion, an IL-2 toxic small molecule conjugate, an IL-2R antagonistic antibody, an IL-2R partial agonist antibody, an antibody-chimeric fusion molecule, an IL-2R antibody toxic small molecule conjugate, a single chain variant of such IL-2R antibodies, or an antagonist or partial agonist of an IL-2R. In some aspects, the inhibitor is an antagonist or partial agonist of the alpha chain of IL-2R, of the beta chain of IL-2R, or the gamma chain of IL-2R.

Additional examples include small molecule inhibitors or peptide inhibitors of the downstream signaling molecules, e.g. Jak1, Jak3, Stat5a, Stat5b, Lck, and Syk. In some embodiments, the inhibitor is an antagonist or partial agonist of Jak1, Jak3, Stat5a, Stat5b, Lck, or Syk.

An exemplary cytokine IL-2 fusion protein includes ONTAK®, an IL-2-diptheria toxin chimera.

An exemplary IL-2 pathway inhibitor includes basiliximab, a chimeric mouse-human monoclonal antibody to CD25 (the alpha chain of the IL-2R). Basiliximab competes with the IL-2 cytokine to bind to the IL-2 receptor on the surface of the activated T lymphocytes and thus prevents the receptor from signaling, ultimately mitigating or preventing antibody production.

Additional exemplary IL-2 pathway inhibitors include daclizumab, a humanized monoclonal antibody that also binds to CD25, preventing or mitigating the production of antibodies.

Further exemplary IL-2 pathway inhibitors include Mikbeta-1, an anti-CD122 monoclonal antibody.

Additional IL-2 pathway inhibitors will become commercially available and it is contemplated that such inhibitors can be used according to the methods provided herein.

Likewise, research grade IL-2 pathway inhibitors are contemplated as useful according to the methods provided herein.

Exemplary mTOR inhibitors include rapamycin and analogs thereof (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Exemplary TGF-β signaling agents include TGF-β ligands (e.g., activin A, GDF1, GDF11, bone morphogenic proteins, nodal, TGF-βs) and their receptors (e.g., ACVR1B, ACVR1C, ACVR2A, ACVR2B, BMPR2, BMPR1A, BMPR1B, TGFβRI, TGFβRII), R-SMADS/co-SMADS (e.g., SMAD1, SMAD2, SMAD3, SMAD4, SMAD5, SMAD8), and ligand inhibitors (e.g, follistatin, noggin, chordin, DAN, lefty, LTBP1, THBS1, Decorin).

Exemplary inhibitors of mitochondrial function include atractyloside (dipotassium salt), bongkrekic acid (triammonium salt), carbonyl cyanide m-chlorophenylhydrazone, carboxyatractyloside (e.g., from *Atractylis gummifera*), CGP-37157, (−)-Deguelin (e.g., from *Mundulea sericea*), F16, hexokinase II VDAC binding domain peptide, oligomycin, rotenone, Ru360, SFK1, and valinomycin (e.g., from *Streptomyces fulvissimus*) (EMD4Biosciences, USA).

Exemplary P38 inhibitors include SB-203580 (4-(4-Fluorophenyl)-2-(4-methylsulfinylphenyl)-5-(4-pyridyl)1H-imidazole), SB-239063 (trans-1-(4hydroxycyclohexyl)-4-(fluorophenyl)-5-(2-methoxy-pyrimidin-4-yl) imidazole), SB-220025 (5-(2amino-4-pyrimidinyl)-4-(4-fluorophenyl)-1-(4-piperidinyl)imidazole)), and ARRY-797.

Exemplary NF (e.g., NK-κβ) inhibitors include IFRD1, 2-(1,8-naphthyridin-2-yl)-Phenol, 5-aminosalicylic acid, BAY 11-7082, BAY 11-7085, CAPE (Caffeic Acid Phenethylester), diethylmaleate, IKK-2 Inhibitor IV, IMD 0354, lactacystin, MG-132 [Z-Leu-Leu-Leu-CHO], NFκB Activation Inhibitor III, NF-κB Activation Inhibitor II, JSH-23, parthenolide, Phenylarsine Oxide (PAO), PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MG-132, sodium salicylate, triptolide (PG490), wedelolactone.

Exemplary adenosine receptor agonists include CGS-21680 and ATL-146e.

Exemplary prostaglandin E2 agonists include E-Prostanoid 2 and E-Prostanoid 4.

Exemplary phosphodiesterase inhibitors (non-selective and selective inhibitors) include caffeine, aminophylline, IBMX (3-isobutyl-1-methylxanthine), paraxanthine, pentoxifylline, theobromine, theophylline, methylated xanthines, vinpocetine, EHNA (erythro-9-(2-hydroxy-3-nonyl) adenine), anagrelide, enoximone (PERFAN™), milrinone, levosimendon, mesembrine, ibudilast, piclamilast, luteolin, drotaverine, roflumilast (DAXAS™, DALIRESP™), sildenafil (REVATION®, VIAGRA®), tadalafil (ADCIRCA®, CIALIS®), vardenafil (LEVITRA®, STAXYN®), udenafil, avanafil, icariin, 4-methylpiperazine, and pyrazolo pyrimidin-7-1.

Exemplary proteasome inhibitors include bortezomib, disulfiram, epigallocatechin-3-gallate, and salinosporamide A.

Exemplary kinase inhibitors include bevacizumab, BIBW 2992, cetuximab (ERBITUX®), imatinib (GLEEVEC®), trastuzumab (HERCEPTIN®), gefitinib (IRESSA®), ranibizumab (LUCENTIS®), pegaptanib, sorafenib, dasatinib, sunitinib, erlotinib, nilotinib, lapatinib, panitumumab, vandetanib, E7080, pazopanib, mubritinib.

Exemplary glucocorticoids include hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Exemplary retinoids include retinol, retinal, tretinoin (retinoic acid, RETIN-A®), isotretinoin (ACCUTANE®, AMNESTEEM®, CLARAVIS®, SOTRET®), alitretinoin (PANRETIN®), etretinate (TEGISON™) and its metabolite acitretin (SORIATANE®), tazarotene (TAZORAC®, AVAGE®, ZORAC®), bexarotene (TARGRETIN®), and adapalene (DIFFERIN®).

Exemplary cytokine inhibitors include IL1ra, IL1 receptor antagonist, IGFBP, TNF-BF, uromodulin, Alpha-2-Macroglobulin, Cyclosporin A, Pentamidine, and Pentoxifylline (PENTOPAK®, PENTOXIL®, TRENTAL®).

Exemplary peroxisome proliferator-activated receptor antagonists include GW9662, PPARγ antagonist III, G335, T0070907 (EMD4Biosciences, USA).

Exemplary peroxisome proliferator-activated receptor agonists include pioglitazone, ciglitazone, clofibrate, GW1929, GW7647, L-165,041, LY 171883, PPARγ activator, Fmoc-Leu, troglitazone, and WY-14643 (EMD4Biosciences, USA).

Exemplary histone deacetylase inhibitors include hydroxamic acids (or hydroxamates) such as trichostatin A, cyclic tetrapeptides (such as trapoxin B) and depsipeptides, benzamides, electrophilic ketones, aliphatic acid compounds such as phenylbutyrate and valproic acid, hydroxamic acids such as vorinostat (SAHA), belinostat (PXD101), LAQ824, and panobinostat (LBH589), benzamides such as entinostat (MS-275), CI994, and mocetinostat (MGCD0103), nicotinamide, derivatives of NAD, dihydrocoumarin, naphthopyranone, and 2-hydroxynaphaldehydes.

Exemplary calcineurin inhibitors include cyclosporine, pimecrolimus, voclosporin, and tacrolimus.

Exemplary phosphatase inhibitors include BN82002 hydrochloride, CP-91149, calyculin A, cantharidic acid, cantharidin, cypermethrin, ethyl-3,4-dephostatin, fostriecin sodium salt, MAZ51, methyl-3,4-dephostatin, NSC 95397, norcantharidin, okadaic acid ammonium salt from prorocentrum concavum, okadaic acid, okadaic acid potassium salt, okadaic acid sodium salt, phenylarsine oxide, various phosphatase inhibitor cocktails, protein phosphatase 1C, protein phosphatase 2A inhibitor protein, protein phosphatase 2A1, protein phosphatase 2A2, sodium orthovanadate.

Administration and Formulations

The immunosuppressants are typically administered to NHPs used in preclinical trials. Exemplary NHPs include, but are not limited to cynomolgus and rhesus macaques; marmosets, tamarins, spider monkeys, owl monkeys, vervet monkeys, squirrel monkeys, and baboons.

In some embodiments, the immunosuppressant is co-administered with the immunogenic therapeutic molecule to reduce, mitigate, or prevent the formation of ADA in a NHP administered the immunogenic therapeutic molecule. "Co-administration" as used in this instance refers to administration of the immunosuppressant and the immunogenic therapeutic molecule. According to certain embodiments of the present disclosure, the immunosuppressant and the immunogenic therapeutic molecule may be administered to the NHP at the same time, or at a different point in time, e.g., on different days separated by a predetermined interval (e.g., hours, days, weeks or months over a defined time course). The methods according to this aspect of the disclosure comprise sequentially administering to a subject one dose or multiple doses of the immunosuppressant and one dose or multiple doses of the immunogenic therapeutic molecule. In addition, the immunosuppressant can be administered prior to or after administration of the immunogenic therapeutic molecule.

In some embodiments, two or more immunosuppressants are co-administered. For example, co-administration of an IL-2 pathway inhibitor and rapamycin (or a rapamycin analog) to a NHP can elicit a tolerogenic effect. "Co-administration" as used in this instance refers to administration of two or more immunosuppressants, along with administration of the immunogenic therapeutic molecule. According to certain embodiments of the present disclosure, the two or more immunosuppressants may be administered to the NHP at the same time, or at a different point in time, e.g., on different days separated by a predetermined interval (e.g., hours, days, weeks or months over a defined time course). The methods according to this aspect of the disclosure comprise sequentially administering to a subject one dose or multiple doses of a first immunosuppressant and one dose or multiple doses of a second immunosuppressant. In addition, a first immunosuppressant can be administered prior to or after administration of a second immunosuppressant.

In some embodiments, the immunosuppressants provided herein are formulated with synthetic nanocarriers. In some embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition to the one or more polymers. As another example, in one embodiment, where the synthetic nanocarrier is made up of one or more lipids, the immunosuppressant is again in addition to the one or more lipids. In some aspects, such as where the material of the synthetic nanocarrier also results in a tolerogenic effect, the immunosuppressant is an element present in addition to the material of the synthetic nanocarrier that results in a tolerogenic effect. The immunosuppressant can be coupled to the nanocarrier.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles.

Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. In some embodiments, synthetic nanocarriers may possess an aspect ratio greater than 1:1, 1:1.2, 1:1.5, 1:2, 1:3, 1:5, 1:7, or greater than 1:10. In some embodiments, the mean of a particle size distribution obtained using dynamic light scattering of the synthetic nanocarriers of the first and/or second population is a diameter greater than 100 nm. In another embodiment, the diameter is greater than 150 nm. In another embodiment, the diameter is greater than 200 nm. In another embodiment, the diameter is greater than 250 nm. In another embodiment, the diameter is greater than 300 nm.

Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), or (11) apoptotic cells, apoptotic bodies or the synthetic or semisynthetic mimics disclosed in U.S. Publication 2002/0086049.

In some embodiments, administration of an immunosuppressant, for example, an IL-2 pathway inhibitor, in accordance with the methods provided herein decreases the probability of an incidence of ADA against an immunogenic therapeutic molecule.

In some embodiments, administration of an immunosuppressant, for example, an IL-2 pathway inhibitor, in accordance with the methods provided herein decreases mean antibodies titers to an immunogenic therapeutic molecule. An antibody response can be assessed by determining one or more antibody titers. "Antibody titer" means a measurable level of antibody production. Methods for measuring antibody titers are known in the art and include Enzyme-linked Immunosorbent Assay (ELISA). In embodiments, the antibody response can be quantitated, for example, as the number of antibodies, concentration of antibodies or titer. The values can be absolute or they can be relative. Assays for quantifying an antibody response include antibody capture assays, enzyme-linked immunosorbent assays (ELISAs), inhibition liquid phase absorption assays (ILPAAs), rocket immunoelectrophoresis (RIE) assays and line immunoelectrophoresis (LIE) assays. When an antibody response is compared to another antibody response the same type of quantitative value (e.g., titer) and method of measurement (e.g., ELISA) is preferably used to make the comparison.

In some embodiments, administration of an immunosuppressant to an NHP in accordance with the methods provided herein decreases the probability of the incidence of an undesired immune response and/or decreases the intensity of an undesired immune response, in particular, when the NHP is administered a therapeutic composition having an otherwise immunogenic therapeutic molecule.

In some embodiments, administration of an IL-2 pathway inhibitor to an NHP in accordance with the methods provided herein decreases the probability of the incidence of an undesired immune response and/or decreases the intensity of an undesired immune response, in particular, when the NHP is administered a therapeutic composition having an otherwise immunogenic therapeutic molecule.

The undesired immune response may be the generation ADA, CD4+ T cell proliferation and/or activity or B cell proliferation and/or activity or combinations thereof.

In some embodiments, administration of an immunosuppressant in accordance with the methods provided herein mitigates or decreases the formation of ADA to an immunogenic therapeutic molecule.

In some embodiments, administration of an immunosuppressant in accordance with the methods provided herein prevents formation of ADA to an immunogenic therapeutic molecule.

In some embodiments, administration of an IL-2 pathway inhibitor in accordance with the methods provided herein mitigates or decreases the formation of ADA to an immunogenic therapeutic molecule.

In some embodiments, administration of an IL-2 pathway inhibitor in accordance with the methods provided herein prevents formation of ADA to an immunogenic therapeutic molecule.

In some aspects, the probability that an immune response will be elicited by the immunogenic therapeutic molecule may be decreased such that the probability is no greater than about 1%. In some aspects, the probability that an immune response will be elicited by the immunogenic therapeutic molecule may be decreased such that the probability is no greater than about 5%. In some aspects, the probability that an immune response will be elicited by the immunogenic therapeutic molecule may be decreased such that the probability is no greater than about 10%. In some aspects, the probability that an immune response will be elicited by the immunogenic therapeutic molecule may be decreased such that the probability is no greater than about 20%. In some aspects, the probability that an immune response will be elicited by the immunogenic therapeutic molecule may be decreased such that the probability is no greater than about 30%. In some aspects, the probability that an immune response will be elicited by the immunogenic therapeutic molecule may be decreased such that the probability is no greater than about 40%. In some aspects, the probability that an immune response will be elicited by the immunogenic therapeutic molecule may be decreased such that the probability is no greater than about 50%. In some aspects, the probability that an immune response will be elicited by the immunogenic therapeutic molecule may be decreased such that the probability is no greater than about 60%. In some aspects, the probability that an immune response will be elicited by the immunogenic therapeutic molecule may be decreased such that the probability is no greater than about 70%. In some aspects, the probability that an immune response will be elicited by the immunogenic therapeutic molecule may be decreased such that the probability is no greater than about 80%. In some aspects, the probability that an immune response will be elicited by the immunogenic therapeutic molecule may be decreased such that the probability is no greater than about 90%.

In some aspects, antibody titers may be decreased at least by about 10% when compared to a control. In some aspects, antibody titers may be decreased at least by about 20% when compared to a control. In some aspects, antibody titers may be decreased at least by about 30% when compared to a control. In some aspects, antibody titers may be decreased at least by about 40% when compared to a control. In some aspects, antibody titers may be decreased at least by about 50% when compared to a control. In some aspects, antibody titers may be decreased at least by about 60% when compared to a control. In some aspects, antibody titers may be decreased at least by about 70% when compared to a control. In some aspects, antibody titers may be decreased at least by about 80% when compared to a control. In some aspects, antibody titers may be decreased at least by about 90% when compared to a control.

Any effective form of an immunosuppressant may be used according to the methods provided herein. For example, the IL-2 pathway inhibitor used can be an antibody or fragment thereof derived from the same species or can be from a different species, or may be chimeric, for example, from a mouse, a human, or a NHP.

The immunosuppressant can be linked to or formulated with a vehicle in order to enhance the activity, half-life, solubility, and so forth of the molecule.

The term "vehicle" refers to a molecule or formulation that prevents degradation and/or increases half-life, reduces toxicity, or increases biological activity of the IL-2 pathway inhibitor. Exemplary vehicles include an Fc domain, a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide (e.g., dextran); or any natural or synthetic protein, polypeptide or peptide.

Exemplary vehicles include synthetic nanocarriers. In one embodiment, the synthetic nanocarrier comprises lipid nanoparticles, polymeric nanoparticles, metallic nanoparticles, surfactant-based emulsions, dendrimers, buckyballs, nanowires, virus-like particles or peptide or protein particles. In another embodiment, the synthetic nanocarriers comprise lipid nanoparticles. In yet another embodiment, the synthetic nanocarriers comprise liposomes. In still another embodiment, the synthetic nanocarriers comprise metallic nanoparticles. In a further embodiment, the metallic nanoparticles comprise gold nanoparticles. In yet a further embodiment, the synthetic nanocarriers comprise polymeric nanoparticles. In another embodiment, the polymeric nanoparticles comprise polymers that are non-methoxy-terminated, pluronic polymers. In still a further embodiment, the polymeric nanoparticles comprise a polyester, a polyester coupled to a polyether, polyamino acid, polycarbonate, polyacetal, polyketal, polysaccharide, polyethyloxazoline or polyethyleneimine. In another embodiment, the polyester comprises a poly(lactic acid), poly(glycolic acid), poly(lactic-co-glycolic acid) or polycaprolactone. In yet another embodiment, the polymeric nanoparticles comprise a polyester and a polyester coupled to a polyether. In another embodiment, the polyether comprises polyethylene glycol or polypropylene glycol.

In some embodiments, the IL-2 pathway inhibitor comprises the cytokine IL-2 or variants thereof fused to a vehicle polypeptide (e.g. immunoglobulin region) or conjugated to a small molecule either directly or through one or more linker moieties. In some embodiments, the IL-2 pathway inhibitor is a super agonist, effectively marking the targeted cell for destruction by apoptosis or necrosis. In some embodiments, the inhibitor is a variant of a cytokine IL-2 conjugate molecule that binds the IL-2R wherein such binding induces deletion of the IL-2R bearing cell through apoptosis, necrosis, autophagy or other mechanism leading to partial, transient or permanent elimination of IL-2R bearing cells from the animal.

In some embodiments, the IL-2 pathway inhibitor comprises an IL-2 domain that binds IL-2R and partially or completely inhibits immune responses mediated by the IL-2R pathway. Other polypeptides useful in the invention include fragments which encompass at least a portion of IL-2 or an IL-2R extracellular domain, which fragments bind the IL-2R or IL-2 cytokine respectively and partially or completely inhibit immune responses mediated through the IL-2R pathway.

In some embodiments, the IL-2 pathway inhibitor includes variants having a substitution, deletion or insertion of one or more amino acids in the IL-2 sequence. As examples, an IL-2 variant may have a substitution of different amino acids as described in publication PMID: 25992859. Exemplary other IL-2 variants are described in publication PMID: 22446627. These published IL-2 variants are exemplary of the methods described herein to inhibit ADA formation in response to treatment with a therapeutic agent. These and other IL-2 variants alter normal receptor binding and signal transduction.

In some embodiments, the above-mentioned IL-2 variants are fused to a vehicle such as an immunoglobulin constant region Fc domain.

The term "Fc domain" or "Fc" refers to molecule or sequence comprising the sequence of a non-antigen-binding fragment of a whole antibody, whether in monomeric or multimeric form. An "Fc domain" or "Fc" may include a "native Fc" or an "Fc variant". The original immunoglobulin source of the native Fc is preferably of NHP origin and may be any of the immunoglobulins. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference.

The Fc may be bound in any effective place of the protein, including, for example at the N terminus or at the C terminus of the IL-2 pathway inhibitor molecule. The Fc may also be bound elsewhere directly onto the protein or via an effective linker.

The immunosuppressant may be administered in any effective manner. An effective manner is any manner that provides a statistically significant modulation of the immune response in accordance with an embodiment of the present invention. An effective manner of administration can be determined by those of skill in the art in accordance with the teachings provided herein, while also taking into consideration the condition to be treated, the immunogenic therapeutic molecule to be administered, the form, dose, pharmacokinetic characteristics, manner and regimen of the immunosuppressant and immunogenic therapeutic molecule administrated, the age and condition of the NHP, and other variables known to those of skill in the art.

The immunosuppressant, such as an IL-2 pathway inhibitor, may be administered in any effective dose. Unless otherwise specified or required by the context, as used herein an effective dose of an immunosuppressant is any dose that provides a statistically significant modulation of the immune response in accordance with an embodiment of the present invention. An effective dose can be determined by those of skill in the art in accordance with the teachings provided herein, while also taking into consideration the condition to be treated, the immunogenic therapeutic molecule to be administered, the form, dose, pharmacokinetic characteristics, manner and regimen of an immunosuppressant and immunogenic therapeutic molecule administrated, the age and condition of the NHP, and other variables known to those of skill in the art.

The effective amount of an immunosuppressant, for example, an IL-2 pathway inhibitor, to be employed will depend, for example, upon the context and objectives, for example, the objectives of the pre-clinical trial or NHP trial. One skilled in the art will appreciate that the appropriate dosage levels will vary depending, in part, upon the immunosuppressant delivered, the nature of the immunogenic response for which the immunosuppressant is being used, the route of administration, and the size (body weight, body surface or organ size) and/or condition (the age and general health) of the NHP. In certain embodiments, investigators/veterinarians may titer the dosage and modify the route of administration to obtain the optimal ADA mitigating effect. A typical dosage may range from about 0.1 mg/kg to up to about 100 mg/kg or more, depending on the factors mentioned above. In some embodiments, the dosage may range from 0.1 mg/kg up to about 30 mg/kg; from 1 mg/kg up to about 30 mg/kg; or from 5 mg/kg up to about 30 mg/kg. In some embodiments, the effective amount of the immunosuppressant or inhibitor is from about 0.1 mg/kg to about 100 mg/kg of the body weight of the NHP. In some embodiments, the effective amount of the immunosuppressant or inhibitor is from about 1 mg/kg to about 100 mg/kg of the body weight of the NHP. In some embodiments, the effective amount of the immunosuppressant or inhibitor is from about 10 mg/kg to about 100 mg/kg of the body weight of the NHP. In some embodiments, the effective amount of the immunosuppressant or inhibitor is from about 10 mg/kg to about 50 mg/kg of the body weight of the NHP.

An "effective amount" in the context of a composition or dosage form for administration to a subject refers to an amount of the composition or dosage form that produces one or more desired immune responses in the subject, for example, a reduction in the amount of ADA, or the generation of a tolerogenic immune response (e.g, a reduction in the proliferation, activation, induction, recruitment of antigen-specific CD4+ T cells or antigen-specific B cells or a reduction in the production of antigen-specific antibodies). Therefore, in some embodiments, an effective amount is any amount of a composition provided herein that produces one or more of these desired immune responses. The amount can be one that a clinician or veterinarian would believe may have a clinical benefit when administered to a NHP to induce antigen-specific tolerization. The amount can be one that a clinician or veterinarian would believe may have a clinical benefit when administered to a NHP to reduce or mitigate an undesired immune response, e.g. reduce ADA formation.

An effective amount can involve only reducing the level of an undesired immune response, although in some embodiments, it involves preventing an undesired immune response altogether. An effective amount can also involve delaying the occurrence of an undesired immune response. An amount that is effective can also be an amount of a composition provided herein that produces a desired therapeutic endpoint or a desired therapeutic result. Effective amounts, in some aspects, result in a tolerogenic immune response in a subject to an antigen. The achievement of any of the foregoing can be monitored by routine methods.

In some embodiments of any of the compositions and methods provided, the effective amount is one in which the desired immune response persists in the subject for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer. In other embodiments of any of the compositions and methods provided, the effective amount is one which produces a measurable desired immune response, for example, a measurable decrease in an immune response (e.g., to a specific antigen), for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer.

The immunosuppressant may be administered in any effective regimen. An effective regimen is any regimen that provides a statistically significant modulation of the immune response in accordance with an embodiment of the present invention. An effective regimen of administration can be determined by those of skill in the art in accordance with the teachings provided herein, while also taking into consideration the condition for which the immunogenic therapeutic molecule is to be administered, the form, dose, pharmacokinetic characteristics, manner and regimen of the immunosuppressant and immunogenic therapeutic molecule administrated, the age and condition of the NHP, and other variables known to those of skill in the art. The immunosuppressant may be administered prior to administration of the immunogenic therapeutic molecule, after administration of the immunogenic therapeutic molecule or contemporaneous with the administration of the immunogenic therapeutic molecule. In addition, the immunosuppressant may be administered more, less, or the same amount of times as the immunogenic therapeutic molecule.

Dosing frequency will depend upon the pharmacokinetic parameters of the particular immunosuppressant composition being used and the pharmacokinetic parameters of the particular immunogenic therapeutic molecule being used. Typically, the composition is administered until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

For example, an IL-2 pathway inhibitor can be administered once daily, every other day, every three days, every 5 days, once weekly, bi-weekly, once every 10 days, every two weeks, every three weeks, every 20 days, or once a month, depending on the half life and the dosage amount of the inhibitor, as well as the treatment regimen of the potentially immunogenic therapeutic being tested. Alternatively, or in addition, the IL-2 pathway inhibitor can be administered as often or as little as is necessary to minimize or prevent the formation of ADA, or as often or as little as is necessary to maintain the target protein (IL-2, CD25, CD122, CD132, jak1, jak3 stat5b, stat5a, syk, lck) at a level that mitigates or prevents the formation of ADA, or as often or as little as is necessary to disrupt the IL-2 signal transduction pathway and mitigate or prevent the formation of ADA.

The immunosuppressant and the potentially immunogenic therapeutic agent can be administered simultaneously or sequentially, in one dose or in several doses, possibly according to a dosing regimen. According to certain embodiments of the present disclosure, an immunosuppressant (or a pharmaceutical composition comprising the immunosuppressant) and the therapeutic agent may be administered to the subject at the same time, or at a different point in time, e.g., on different days separated by a predetermined interval (e.g., hours, days, weeks or months over a defined time course). The methods according to this aspect of the disclosure comprise sequentially administering to a subject one dose or multiple doses of an immunosuppressant as disclosed herein and one dose or multiple doses of the therapeutic agent. In addition, an immunosuppressant can be administered prior to or after administration of the therapeutic agent.

The compositions used according to the methods provided herein may be formulated in any effective manner. An effective formulation for the administration of an immunosuppressant such as an IL-2 pathway inhibitor and the immunogenic therapeutic molecule can be determined by those of skill in the art in accordance with the teachings provided herein, while also taking into consideration the condition to be treated, the immunogenic therapeutic molecule to be administered, the form, dose, pharmacokinetic characteristics, manner and regimen of the IL-2 pathway inhibitor and immunogenic therapeutic molecule administrated, the age and condition of the NHP, and other variables known to those of skill in the art. The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also can be desirable to use an immunosuppressant such as an IL-2 pathway inhibitor pharmaceutical compositions ex vivo. In such instances, cells, tissues or organs that have been removed from the NHP are exposed to an IL-2 pathway inhibitor pharmaceutical compositions after which the cells, tissues and/or organs are subsequently implanted back into the NHP.

In particular, an IL-2 pathway inhibitor can be delivered by implanting certain cells that have been genetically engineered, using methods such as those known in the art, to express and secrete the polypeptide. In other embodiments, such cells may be animal or human cells, and may be autologous, heterologous, or xenogeneic. In other embodiments, the cells may be immortalized.

In other embodiments, pharmaceutical compositions are provided comprising an effective amount of an IL-2 pathway inhibitor together with a pharmaceutically acceptable diluent, carrier, solubilizer, emulsifier, preservative and/or adjuvant. Acceptable formulation materials are nontoxic to recipients at the dosages and concentrations employed. In another embodiment, pharmaceutical compositions comprising an effective amount of an IL-2 pathway inhibitor-Fc are provided.

In another embodiment, pharmaceutical compositions are provided comprising an effective amount of an IL-2 pathway inhibitor and an effective amount of an immunogenic therapeutic molecule together with a pharmaceutically acceptable diluent, carrier, solubilizer, emulsifier, preservative and/or adjuvant.

Acceptable formulation materials are nontoxic to recipients at the dosages and concentrations employed. In another embodiment, pharmaceutical compositions comprising an effective amount of an IL-2 pathway inhibitor-Fc and an effective amount of an immunogenic therapeutic molecule are provided. In one embodiment, the compositions may be in the form of a mixture of an IL-2 pathway inhibitor and the immunogenic therapeutic molecule. The compositions may be an effective form of a single molecule including an effective form of an IL-2 pathway inhibitor and an effective form of an immunogenic therapeutic molecule.

In another embodiment, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See Remington's Pharmaceutical Sciences, 18$^{th}$ Edition, (A. R. Gennaro, ed.), 1990, Mack Publishing Company.

In other embodiments, the optimal pharmaceutical composition will be determined by one skilled in the art depending upon, for example, the intended route of administration, delivery format and desired dosage. See, for example, Remington's Pharmaceutical Sciences, supra. In other embodiments, such compositions may influence the physical state, stability, rate of in vivo release and rate of in vivo clearance of an IL-2 pathway inhibitor.

In other embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In other embodiments of the invention, IL-2 pathway inhibitor compositions may be prepared for storage by mixing the selected composition having the desired degree of purity with optional formulation agents (Remington's Pharmaceutical Sciences, supra) in the form of a lyophilized cake or an aqueous solution. Further, in certain embodiments, an IL-2 pathway inhibitor may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such by ingestion. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the compositions for use in methods provided herein may be provided in the form of a pyrogen-free, parenterally acceptable aqueous solution comprising an IL-2 pathway inhibitor in a pharmaceutically acceptable vehicle. A particularly suitable vehicle for parenteral injection is sterile distilled water in which an IL-2 pathway inhibitor is formulated as a sterile, isotonic solution, which is properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired molecule.

Pharmaceutical compositions of the invention can be formulated for inhalation. In these embodiments, an IL-2 pathway inhibitor, for example, is advantageously formulated as a dry, inhalable powder. In other embodiments, IL-2 pathway inhibitor inhalation solutions may also be formulated with a propellant for aerosol delivery. In other embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that immunosuppressant formulations can be administered orally. For example, IL-2 pathway inhibitors administered in this fashion can be formulated with or without carriers customarily used in the compounding of solid dosage forms such as tablets and capsules. In other embodiments, a capsule may be designed to release the active portion of the formulation at the point in the gastrointestinal tract when bioavailability is maximized and presystemic degradation is minimized. Additional agents can be included to facilitate absorption. Diluents, flavorings, low melting point waxes, vegetable oils, lubricants, suspending agents, tablet disintegrating agents, and binders may also be employed.

A pharmaceutical composition of the invention is preferably provided to comprise an effective quantity of an immunosuppressant such as an IL-2 pathway inhibitor in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving immunosuppressants in sustained or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 22:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., supra) or poly-D(−)-3-hydroxybutyric acid (European Patent Application Publication No. EP 133,988).

Sustained release compositions may also include liposomes that can be prepared by any of several methods known in the art. See e.g., Eppstein et al., 1985, Proc. Natl. Acad. Sci. USA 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper that is capable of being pierced by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Potentially Immunogenic Therapeutic Molecules

Administration of an immunosuppressant composition may be used in accordance with the methods provided herein, either alone or in combination, to modulate the immune response against any immunogenic therapeutic molecule for which they are effective.

Administration of an IL-2 pathway inhibitor composition may be used in accordance with the methods provided herein, either alone or in combination, to modulate the immune response against any immunogenic therapeutic molecule for which they are effective.

Unless otherwise required by the context, as used herein the term immunogenic therapeutic molecule means any molecule having a therapeutic or in vivo diagnostic use and that is capable of generating an immune response when administered to a NHP. Whether a molecule is capable of generating an immune response may be determined in any effective manner, including empirically, by molecular modeling, structural analysis and the like. See, e.g., Koren, et al., Current Pharmaceutical Biotechnology 3:349-360 (2002).

Immunogenic therapeutic molecules in accordance with an embodiment of the present invention are therapeutic proteins. These include, for example hormones, enzymes, cytokines, antibodies, receptors and antagonists, growth factors, interferons, and the like. See, e.g., Koren, et al., Current Pharmaceutical Biotechnology 3:349-360 (2002); Porter, S., Journal of Pharmaceutical Sciences 90(1):1-11 (2001); Rosenberg, A. S., Immunogenicity of Therapeutic Biological Products, Dev. Biol. Basel, Karger, 2003, vol. 112, pp. 15-21; Schellekens, et al., Immunogenicity of Therapeutic Biological Products, Dev. Biol. Basel, Karger, 2003, vol 112, pp. 23-38; Chamberlain, et al., Immunogenicity of Therapeutic Biological Products, Dev. Biol. Basel, Karger, 2003, vol 112, pp. 3-11; Stein, K. F., Biologics 2000—Comparability of Biotechnology Products Dev. Bio. Basel, Karger, 2002, vol. 109, pp. 15-23; Herzyk, D. J., Current Opinion in Molecular Therapeutics 5(2):167-171 (2003); Schroff, et al., Human anti-murine immunoglobulin responses in patients receiving monoclonal antibody therapy, Cancer Res., 45(2):879-85 (1985); Isaacs, J. D., The antiglobulin response to therapeutic antibodies, Semin Immunol., 2(6):449-56 (1990) (all of which are incorporated herein by reference as if fully set forth herein). In other embodiments, at least part of the potentially immunogenic therapeutic molecules comprises a non-human or non-NHP component. Said non-human component may be from another organism other than a human, such as a mouse, or it may be the product of chemical synthesis, for example, a non-naturally occurring amino acid or a synthetic water soluble polymer.

Potentially immunogenic therapeutic molecules can be a class of immunogenic therapeutic proteins, for example, immunoglobulins. Pooled human IgG from human donors can be administered in a tolerizing protocol as provided herein, where the NHP develops immune tolerance to the complementarity determining regions (CDR) and framework regions of the human antibodies. These tolerized NHP can then be used to test the immunogenicity of any given therapeutic human antibody as the potential immune response would largely be directed to the novel CDR3 of the therapeutic antibody. Such tolerized NHP would constitute a predictive model for testing the immunogenicity of therapeutic human antibodies and the immune response in these animals would be relevant to human treatment with the same therapeutic human antibodies.

Unless otherwise required by the context, as used herein the term immune response means that detectable serum antibodies specific for the protein of interest are formed, e.g., an overt presence of detectable antibodies.

Methods for determining whether an immune response to a therapeutic molecule has occurred are known to those in the art. Generally, a convenient method for detecting an immune response is by determining levels of ADA in a NHP's sera. Analysis of antibodies in biological fluids may be carried out in any effective manner, including, for example, radioimmunoprecipitation assays (RIA), enzyme linked immunosorbent assays (ELISA), dissociation enhanced lanthanide fluroimmunoassays (DELFIA), and surface plasmon resonance methods. These methods will detect whether an antibody binds to the therapeutic molecule and may also be used to detect whether an antibody will cross-react with other related molecules. For additional details, see Koren et al. supra.

The biological effects of an antibody produced by immune response can most conveniently be determined by a bioassay suitable for the potentially immunogenic therapeutic molecule being administered. Generally, observing a decreased activity when serum from a NHP exhibiting an immune response is added to a bioassay may indicate a neutralizing activity by an antibody.

Specific examples of therapeutic immunogenic molecules described herein include TNF binding proteins and peptides designated mL6-17 and mL63-9 (synthetic peptides which bind to nerve growth factor) fused to an Fc domain. (See published European patent application EP 0 422 339, WO92/16221 and PCT publication no. WO95/34326). WO92/16221 states at page 15: "This invention describes pegylated 30 kDa TNF inhibitor and pegylated IL-1 receptor antagonist. Most preferred pegylated TNF inhibitors include 30 kDa TNF inhibitor wherein the asparagine amino acid residue at position 105 of the native human protein is changed to cysteine using in vitro mutagenesis and pegylation has occurred at the free cysteine at position 105. Other pegylated derivatives of mutated 30 kDa TNF inhibitors include mutations where cysteine has been added at positions 1, 14, 111 and 161. In addition to the singly pegylated muteins, any and all combinations of the various mutations may be included within a single mutein to create altered 30 kDa TNF with more than one free cysteine residue capable of being pegylated."

Other examples of therapeutic immunogenic molecules include proteins for protein replacement or protein supplementation therapy. In another embodiment, the immunogenic molecule comprises a/an infusible or injectable therapeutic protein, enzyme, enzyme cofactor, hormone, blood or blood coagulation factor, cytokine, interferon, growth factor, monoclonal antibody, polyclonal antibody or protein associated with Pompe's disease. In another embodiment, the infusible or injectable therapeutic protein comprises Tocilizumab, alpha-1 antitrypsin, Hematide, albinterferon alfa-2b, Rhucin, tesamorelin, ocrelizumab, belimumab, pegloticase, taliglucerase alfa, agalsidase alfa or velaglucerase alfa. In another embodiment, the enzyme comprises an oxidoreductase, transferase, hydrolase, lyase, isomerase or ligase. In another embodiment, the enzyme comprises an enzyme for enzyme replacement therapy for a lysosomal storage disorder. In another embodiment, the enzyme for enzyme replacement therapy for a lysosomal storage disorder comprises imiglucerase, a-galactosidase A (a-gal A), agalsidase beta, acid a-glucosidase (GAA), alglucosidase alfa, LUMIZYME, MYOZYME, arylsulfatase B, laronidase, ALDURAZYME, idursulfase, ELAPRASE, arylsulfatase B or NAGLAZYME. In another embodiment, the cytokine comprises a lymphokine, interleukin, chemokine, type 1 cytokine or a type 2 cytokine. In another embodiment, the blood and blood coagulation factor comprises Factor I, Factor II, tissue factor, Factor V, Factor VII, Factor VIII, Factor IX, Factor X, Factor Xa, Factor XII, Factor XIII, von Willebrand factor, prekallikrein, high-molecular weight kininogen, fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant or epoetin alfa. In still another embodiment, the therapeutic immunogenic protein is expressed in, by or on cells of a cell-based therapy.

A wide variety of factors can impact on the response of the immune system to a product. Accordingly, in accordance with the present invention the disease type, severity and benefit of treatment should be considered when assessing the risk associated with the immunogenicity of any biological product.

Kits

The invention also provides kits for producing a single-dose administration unit for an IL-2 pathway inhibitor or the like and a single-dose administration unit for an immunogenic therapeutic molecule. The kits of the invention may each contain both a first container having an effective form of an IL-2 pathway inhibitor, for example as a dried protein, a second container having an immunogenic therapeutic composition, a third container having an aqueous formulation for an IL-2 pathway inhibitor dried protein and a fourth container having an aqueous formulation for the immunogenic therapeutic composition. Alternatively, an IL-2 pathway inhibitor and the immunogenic therapeutic composition may be soluble in the same aqueous formulation, in which case only a third container is necessary.

The invention also provides kits for producing a single-dose administration unit for an immunosuppressant and a single-dose administration unit for an immunogenic therapeutic molecule. The kits of the invention may each contain both a first container having an effective form of an immunosuppressant, for example as a dried protein, a second container having an immunogenic therapeutic composition, a third container having an aqueous formulation for an immunosuppressant and a fourth container having an aqueous formulation for the immunogenic therapeutic composition. Alternatively, an immunosuppressant and the immunogenic therapeutic composition may be soluble in the same aqueous formulation, in which case only a third container is necessary.

The invention also provides kits for producing a single-dose administration unit. The kits of the invention may each contain a first container having a dried protein and a second container having an aqueous formulation. In certain embodiments of this invention, kits containing single and multi-chambered pre-filled syringes (e.g., liquid syringes and lyosyringes) are provided.

All references cited in the present disclosure are incorporated by reference in their entirety as if fully set forth herein.

The present invention and the manner in which it may be practiced are further illustrated by the following examples.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided for illustrative purposes only and are not intended to limit the scope of the invention.

Example 1

Administration of a basiliximab loading dose on Day 0 of the NHP preclinical pharmacokinetic study is followed on Day 1 by administration of a basiliximab maintenance dose and the potentially immunogenic therapeutic agent. Basiliximab is dosed approximately every 10 days to maintain a serum concentration at which CD25 is almost completely bound by basiliximab (about 200 ug/mL). The therapeutic agent is dosed at the proscribed interval and dose. In a control group to which the therapeutic agent but not basiliximab is administered, the pharmacokinetic parameters of the therapeutic agent are altered (increased or decreased) due to the development of ADA in some or all of the animals. In the basiliximab treated group, no ADA develops or the level of ADA is sufficiently low such that the pharmacokinetic parameters of the therapeutic agent are unaltered. Because the basiliximab treated NHP do not develop ADA, they may be used in another study with the same or a different potentially immunogenic therapeutic agent.

Example 2

Administration of a basiliximab loading dose on Day 0 of the NHP toxicology study is followed on Day 1 by administration of a basiliximab maintenance dose and the potentially immunogenic therapeutic agent. Basiliximab is dosed approximately every 10 days to maintain a serum concentration at which CD25 is almost completely bound by basiliximab (about 200 ug/mL). The therapeutic agent is dosed at the proscribed interval and dose. In the group administered basiliximab and the therapeutic agent, the animals develop immune mediated drug induced liver injury (DILI). In the group administered the potentially immunogenic therapeutic agent alone, the development of ADA in some or all of the animals prevents the induction of DILI, thus masking a potentially fatal drug associated toxicity. Because administration of basiliximab prevents the development of ADA and thus unmasks immune DILI mediated by the immunogenic therapeutic agent, further development of the therapeutic agent would be halted by the sponsor.

Example 3

Administration of a nanocarrier encapsulated rapamycin (NER) loading dose on Day -2, -1, or 0 of the NHP preclinical pharmacokinetic study is followed on Day 0 by administration the potentially immunogenic therapeutic agent. NER and the therapeutic agent are then co-administered at the proscribed dose and intervals of every 1-4 weeks for as many as 12 weeks, following which the immunogenic therapeutic agent may be administered without NER. In a control group to which the therapeutic agent but not NER is administered, the pharmacokinetic parameters of the therapeutic agent are altered (increased or decreased) due to the development of ADA in some or all of the animals. In the NER treated group, no ADA develops or the level of ADA is sufficiently low such that the pharmacokinetic parameters of the therapeutic agent are unaltered. Because the NER treated NHP do not develop ADA, they may be used in another study with the same or a different potentially immunogenic therapeutic agent.

Example 4

Administration of a nanocarrier encapsulated rapamycin (NER) loading dose on Day -2, -1, or 0 of the NHP toxicology study is followed on Day 0 by administration the potentially immunogenic therapeutic agent. NER and the therapeutic agent are then co-administered at the proscribed dose and intervals of every 1-4 weeks for as many as 12 weeks, following which the immunogenic therapeutic agent may be administered without NER. In the group administered NER and the therapeutic agent, the animals develop immune mediated drug induced liver injury (DILI). In the group administered the potentially immunogenic therapeutic agent alone, the development of ADA in some or all of the animals prevents the induction of DILI, thus masking a potentially fatal drug associated toxicity. Because administration of NER prevents the development of ADA and thus unmasks immune DILI mediated by the immunogenic therapeutic agent, further development of the therapeutic agent would be halted by the sponsor.

Example 5

Administration of a basiliximab and rapamycin loading dose on Day 0 of the NHP preclinical pharmacokinetic study is followed on Day 1 by administration of a basiliximab and rapamycin maintenance doses and the potentially immunogenic therapeutic agent. Basiliximab is dosed approximately every 10 days to maintain a serum concentration at which CD25 is almost completely bound by basiliximab (about 200 ug/mL). Rapamycin is dosed daily or every other day during the course of basiliximab administration to maintain a rapamycin trough level within the range of 4-12 ng/mL. Following this treatment regimen, the immunogenic therapeutic agent may be administered without the immunosuppressant combination. In a control group to which the therapeutic agent but not the immunosuppressant is administered, the pharmacokinetic parameters of the therapeutic agent are altered (increased or decreased) due to the development of ADA in some or all of the animals. In the immunosuppressant treated group, no ADA develops or the level of ADA is sufficiently low such that the pharmacokinetic parameters of the therapeutic agent are unaltered. Because the immunosuppressant treated NHP do not develop ADA, they may be used in another study with the same or a different potentially immunogenic therapeutic agent.

Example 6

Administration of a basiliximab and rapamycin loading dose on Day 0 of the NHP toxicology study is followed on Day 1 by administration of a basiliximab and rapamycin maintenance doses and the potentially immunogenic therapeutic agent. Basiliximab is dosed approximately every 10 days to maintain a serum concentration at which CD25 is almost completely bound by basiliximab (about 200 ug/mL). Rapamycin is dosed daily or every other day during the course of basiliximab administration to maintain a rapamycin trough level within the range of 4-12 ng/mL. Following this treatment regimen, the immunogenic therapeutic agent may be administered without the immunosuppressants. In the group administered immunosuppressants and the therapeutic agent, the animals develop immune mediated drug induced liver injury (DILI). In the group administered the potentially immunogenic therapeutic agent alone, the development of ADA in some or all of the animals prevents the induction of DILI, thus masking a potentially fatal drug associated toxicity. Because administration of rapamycin and basiliximab prevents the development of ADA and thus unmasks immune DILI mediated by the immunogenic therapeutic agent, further development of the therapeutic agent would be halted by the sponsor.

PUBLICATIONS

The publications provided below are incorporated by reference in their entirety.

U.S. Pat. No. 9,180,182 to van Kooyk, et al. Nov. 10, 2015
U.S. Pat. No. 9,175,083 to Cho, et al. Nov. 3, 2015
U.S. Pat. No. 9,133,268, Immunoconjugates with an intracellularly-cleavable linkage
U.S. Pat. No. 9,133,200, Imidazo[1,2-b]pyridazine and imidazo[4,5-b]pyridine derivatives as JAK inhibitors
U.S. Pat. No. 9,109,026, Dual variable domain immunoglobulins and uses thereof
U.S. Pat. No. 8,961,968, Human monoclonal antibodies against CD25
U.S. Pat. No. 8,182,812, Human monoclonal antibodies against CD25
U.S. Pat. No. 7,438,907, Human monoclonal antibodies against CD25
U.S. Pat. No. 7,078,034, In vitro activated γδ lymphocytes
U.S. Pat. No. 6,521,230, CD25 binding molecules
U.S. Pat. No. 6,383,487, Methods of treatment using CD25 binding molecules
U.S. Pat. No. 5,889,160, Human IL-2 receptor.gamma.-chain molecule antibody
U.S. Pat. No. 8,465,739, Stable aqueous pharmaceutical formulations of daclizumab antibodies
U.S. Pat. No. 6,596,853, DNA encoding peptides of IL-2
U.S. Pat. No. 6,168,785, Biological applications of new peptides of IL-2 and derivatives and use as therapeutic agents
U.S. Pat. No. 7,579,439, Modulation of IL-2- and IL-15-mediated T cell responses
U.S. Pat. No. 9,028,830, Antibodies to CD122
U.S. Pat. No. 5,314,995, Therapeutic interleukin-2-antibody based fusion proteins
U.S. Pat. No. 8,759,486, Immunomodulatory interleukin-2 polypeptides and methods of treating melanoma
RE33,252, Hybridoma antibody which inhibits Interleukin 2 activity
U.S. Pat. No. 4,845,198, Hybridoma antibody which binds IL-2 receptor
U.S. Pat. No. 4,772,572, Hybridomas and monoclonal antibodies to human IL-2
U.S. Pat. No. 4,473,493, Hybridoma antibody which inhibits interleukin 2 activity
U.S. Pat. No. 4,411,993, Hybridoma antibody which inhibits interleukin 2 activity
U.S. 2014/0349323, Anti-Drug Antibody Assay
U.S. Pat. No. 8,895,544, Indazoles
U.S. Pat. No. 8,592,368, JAK/STAT inhibitors and MAPK/ERK inhibitors for RSV infection
U.S. Pat. No. 7,423,113, Leptin antagonist
U.S. Pat. No. 6,998,391, Method for treating diseases associated with abnormal kinase activity
U.S. 2016/0256401
Nonclinical safety testing of biopharmaceuticals—Addressing current challenges of these novel and emerging therapies. Brennan et al., Regul Toxicol Pharmacol. 2015 October; 73(1):265-75. doi: 10.1016/j.yrtph.2015.07.019. Epub 2015 Jul. 26.
Impact of anti-drug antibodies in preclinical pharmacokinetic assessment. Thway et al., AAPS J. 2013 July; 15(3):856-63. doi: 10.1208/s12248-013-9484-4. Epub 2013 May 8. PMID: 23653044
Immunogenicity assessment in non-clinical studies. Swanson S J, and Bussiere J. Curr Opin Microbiol. 2012 June; 15(3):337-47. doi: 10.1016/j.mib.2012.05.015. Epub 2012 Jul. 4. Review. PMID: 22770538
Safety evaluation of biological drugs: what are toxicology studies in primates telling us? Baldrick P. Regul Toxicol Pharmacol. 2011 March; 59(2):227-36. doi: 10.1016/j.yrtph.2010.10.005. Epub 2010 Oct. 16. PMID: 20937341
Immunogenicity of therapeutics: a matter of efficacy and safety. Nechansky A, and Kircheis R., Expert Opin Drug Discov. 2010 November; 5(11):1067-79. doi: 10.1517/17460441.2010.514326. Epub 2010 Sep. 1. Review. PMID: 22827745
Chamberlain, P. et al. "An Overview of Scientific and Regulatory Issues for the Immunogenicity of Biological Products." Immunogenicity of Therapeutic Biological Products, Dev. Biol. Basel, Karger 112:3-11 (2003).
Chang, C-C. J. et al. "Evolution of a Cytokine Using DNA Family Shuffling." Nature Biotechnology 17:793-797 (1999).
Herzyk, D. J. "The Immunogenicity of Therapeutic Cytokines." Current Opinion in Molecular Therapeutics 5(2): 167-171 (2003).
Isaacs, J. D. "The Antiglobulin Response to Therapeutic Antibodies." Seminars in Immunology 2(6):449-456 (1990).
Issacs, J. D. "From Bench to Bedside: Discovering Rules for Antibody Design, and Improving Serotherapy with Monoclonal Antibodies." Rheumatology 40:724-738 (2001).
Koren, E. et al. "Immune Responses to Therapeutic Proteins in Humans—Clinical Significance, Assessment and Prediction." Current Pharmaceutical Biotechnology 3(4): 349-360 (2002).
Kurtzman, A. L. et al. "Advances in Directed Protein Evolution by Recursive Genetic Recombination: Applications to Therapeutic Proteins." Current Opinion in Biotechnology 12:361-370 (2001).
Porter, S. "Human Immune Response to Recombinant Human Proteins." J. Pharmaceutical Sciences 90(1):1-11 (2001).
Rosenberg, A. S. "Immunogenicity of Biological Therapeutics: A Hierarchy of Concerns." Immunogenicity of Therapeutic Biological Products, Dev. Biol. Basel, Karger 112:15-21 (2003).
Schellekens, H. et al. "Immunogenicity of Biopharmaceuticals. The European Perspective." Immunogenicity of Therapeutic Biological Products, Dev. Biol. Basel, Karger, 112:23-38 (2003).
Schroff, R. W. et al. "Human Anti-Murine Immunoglobulin Responses in Patients Receiving Monoclonal Antibody Therapy." Cancer Res. 45(2):879-885 (1985).

Stein, K. E. "Immunogenicity: Concepts/Issues/Concerns." Biologics 2000—Comparability of Biotechnology Products Dev. Bio. Basel, Karger 109:15-23 (2002).

Tsutsumi, Y. et al. "Site-Specific Chemical Modification with Polyethylene Glycol of Recombinant Immunotoxin Anti-Tac(Fv)-PE38 (LMB-2) Improves Antitumor Activity and Reduces Animal Toxicity and Immunogenicity." Proc. Natl. Acad. Sci. 97:8548-8553 (2000).

I claim:

1. A method of mitigating formation of anti-drug antibodies (ADA) to an immunogenic therapeutic protein in a non-human primate (NHP), the method comprising administering to the NHP an effective amount of a recombinant anti-CD122 monoclonal antibody that inhibits the binding of IL-2 to its cognate receptor, or an antigen-binding fragment thereof, wherein the anti-CD122 monoclonal antibody is Mik-beta-1 (Mikβ1);

wherein at least one dose of the anti-CD122 antibody or antigen-binding fragment thereof is administered to the NHP within 1 day prior to administration of the immunogenic therapeutic protein, concurrently with the immunogenic therapeutic protein, and/or within 1 day after administration of the immunogenic therapeutic protein, and wherein administration of the antibody or antigen-binding fragment thereof decreases the formation of ADA to the immunogenic therapeutic protein in the NHP.

2. The method of claim 1, wherein the anti-CD122 antibody comprises an antigen-binding fragment thereof of Mikβ1 and a NHP sequence.

3. The method of claim 1 wherein the effective amount of the anti-CD122 antibody or antigen-binding fragment thereof is from about 0.1 mg/kg to about 100 mg/kg of the body weight of the NHP.

4. The method of claim 1, wherein at least one additional dose of the anti-CD122 antibody or antigen-binding fragment thereof is administered 1 day before, during, and/or 1 day after an additional administration of the immunogenic therapeutic protein.

5. The method of claim 1, wherein the anti-CD122 antibody or an antigen-binding fragment thereof is administered at an interval equal to or less than the apparent half-life of the antibody in NHPs.

6. The method of claim 1, wherein the anti-CD122 antibody or antigen-binding fragment thereof is administered once a day or once a week.

7. The method of claim 1, wherein the anti-CD122 antibody or antigen-binding fragment thereof is administered once bi-weekly, once every three weeks, or once every month.

8. The method of claim 1, wherein the anti-CD122 antibody or antigen-binding fragment thereof is administered every other day, every three days, every 5 days, once every 10 days, every two weeks, or every 20 days.

9. The method of claim 1, wherein the anti-CD122 antibody or antigen-binding fragment thereof is administered as often or as little as is necessary to maintain receptor occupancy at a level that mitigates or prevents formation of ADA.

10. The method of claim 1, wherein the immunogenic therapeutic protein is administered in more than one dose, wherein subsequent doses are separated by hours, days, weeks, or months.

11. The method of claim 1, wherein the anti-CD122 antibody or antigen-binding fragment thereof is administered to the NHP within 1 day prior to administration of each dose of the immunogenic therapeutic protein, concurrently with each dose of the immunogenic therapeutic protein, and/or within 1 day after administration of each dose of the immunogenic therapeutic protein.

12. The method of claim 1, further comprising administering to the NHP an effective dose of rapamycin.

13. The method of claim 12, wherein the rapamycin is administered daily or every other day.

14. The method of claim 12, wherein the concentration of rapamycin is maintained at a trough level within the range of 4-12 ng/mL.

* * * * *